US00PP36592P3

(12) United States Plant Patent
Salman

(10) Patent No.: US PP36,592 P3
(45) Date of Patent: Apr. 8, 2025

(54) ***BOUTELOUA* HYBRID PLANT NAMED 'Zig Zag'**

(50) Latin Name: ***Bouteloua* hybrid**
Varietal Denomination: Zig Zag

(71) Applicant: Ava Salman, Sante Fe, NM (US)

(72) Inventor: David Mark Salman, Sante Fe, NM (US)

(73) Assignee: Ava Salman, LLC, Santa Fe, NM (US)

( * ) Notice: Subject to any disclaimer, the term of this patent is extended or adjusted under 35 U.S.C. 154(b) by 0 days.

(21) Appl. No.: 17/803,776

(22) Filed: Nov. 21, 2022

(65) Prior Publication Data

US 2024/0292770 P1 Aug. 29, 2024

(51) Int. Cl.
*A01H 5/12* (2018.01)
*A01H 6/46* (2018.01)

(52) U.S. Cl.
USPC ..... Plt./384
CPC ..... *A01H 6/46* (2018.05)

(58) Field of Classification Search
USPC ..... Plt./384
CPC ..... A01H 5/00; A01H 5/12
See application file for complete search history.

(56) References Cited

U.S. PATENT DOCUMENTS

PP22,048 P2 * 7/2011 Salman ..... A01H 6/46 Plt./384
PP33,101 P2 * 5/2021 Horvath ..... A01H 6/46 Plt./384

OTHER PUBLICATIONS https://santafebotanicalgarden.org/plant-of-the-month-november-2022/; Nov. 1, 2022; 4 pages.*
https://santafebotanicalgarden.org/plant-of-the-month-Nov. 2022/; Nov. 1, 2022; 4 pages.*

* cited by examiner

*Primary Examiner* — Kent L Bell
(74) *Attorney, Agent, or Firm* — Hunt IP Law

(57) ABSTRACT

The new and distinct variety of *Bouteloua* hybrid variety 'Zig Zag' is provided. The variety can be distinguished by its outstanding features of tight, low mounded, and fine textured foliage, with numerous seed heads.

2 Drawing Sheets

Figure 1:
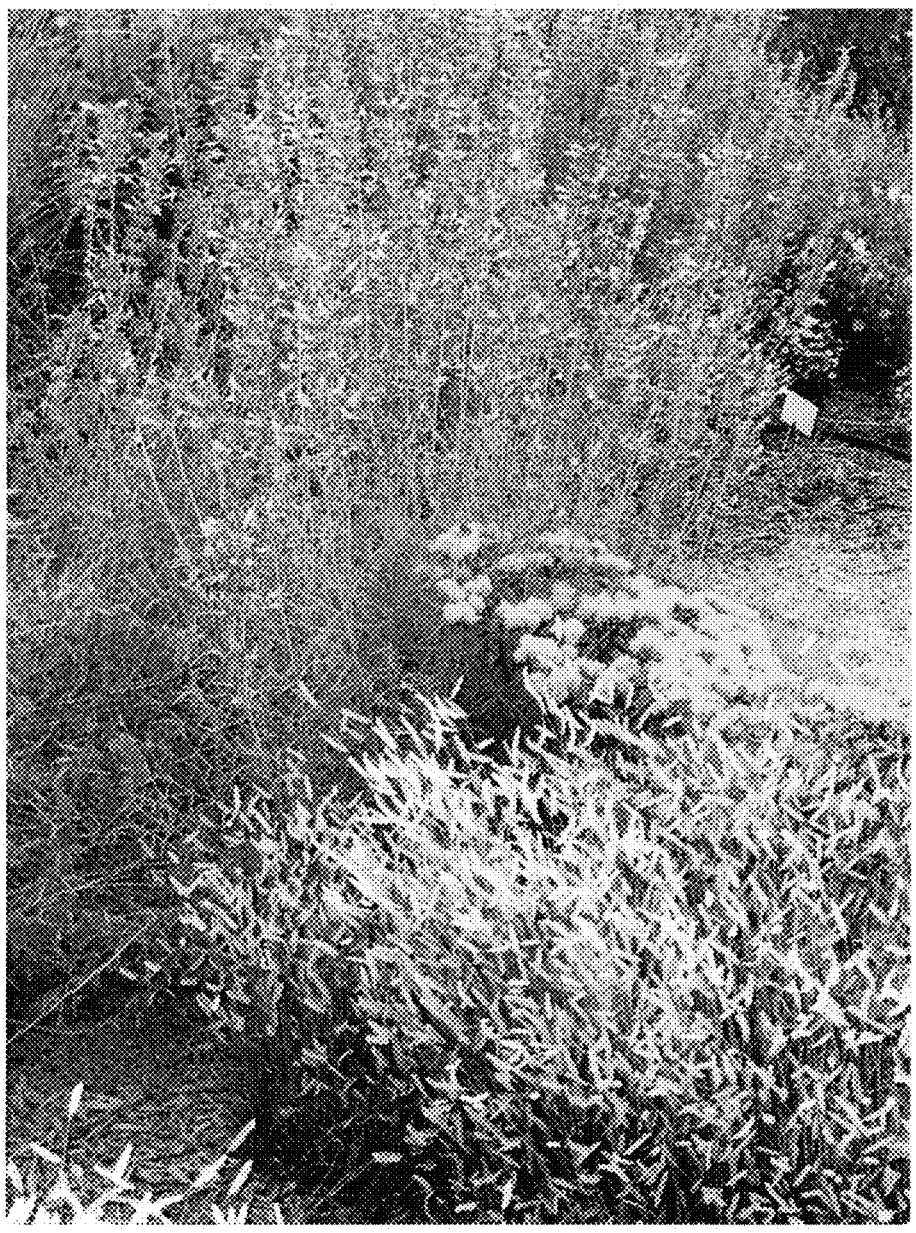

Latin name of the genus and species of the plant claimed: The ornamental plant variety of this invention is botanically identified as *Bouteloua* hybrid.

Variety denomination: The variety denomination is 'Zig Zag'. This plant is not known by any other name or trademark name.

CROSS REFERENCE TO RELATED APPLICATIONS

None.

BACKGROUND OF THE INVENTION

Field of the Invention

The present invention relates to a new and distinct variety of *Bouteloua* hybrid, also known as Blue Grama Grass, which has been given the variety denomination of 'Zig Zag'

BRIEF SUMMARY OF THE INVENTION

The new *Bouteloua* hybrid variety is a selection resulting from a new phenotype discovered growing in a cultivated state. The new variety was found as a unique individual amongst a population of other known plants in a cultivated area. The parentage of the new variety is unknown.

The selection was subsequently evaluated for a number of years in Santa Fe, NM.

The following characteristics of the new variety have been repeatedly observed and can be used to distinguish 'Zig Zag' as a new and distinct variety of *Bouteloua* hybrid plant. Most of these features occur in either *Bouteloua gracilis* or *Bouteloua hirsuta*, though some of them are rare. The combination of features, however, is unique and distinctive. Because of similarities to, and differences from characteristics of *B. gracilis* and *B. hirsuta*, the new variety is designated as a *Bouteloua* hybrid.

1. Plants loosely caespitose, stoloniferous, and comparatively rapidly-spreading;
2. flowering culms very numerous, often forked;
3. leaf blades lacking marginal pustulose-based trichomes and weakly or not at all scabrous on the veins;
4. rachises not prolonged beyond the terminal spikelets on the primary branches of the inflorescence;
5. glumes with long, pustulose-based trichomes; and
6. anthers chartreuse to pale yellow at anthesis.

Asexual reproduction of the new variety by crown division since 2020 at Santa Fe, New Mexico has demonstrated that the new variety reproduces true to type with all of the morphological characteristics, as herein described, firmly fixed and retained through successive generations of such asexual propagation.

Plants of the new variety differ from known variety 'Blonde Ambition' (U.S. Plant Pat. No. 22,048) in the following ways:

1. 'Blonde Ambition' is roughly twice as tall as 'Zig Zag' (28-30" vs. 16-18").
2. 'Zig Zag' has numerous light gray-brown flower heads that "ladder up" the flowering stems, while 'Blonde Ambition' has chartreuse flowers holding 3 to 5 seed heads on top of each flowering stem.
3. 'Zig Zag' flowers/seed heads are half as long as 'Blonde Ambition' and appear chubbier.
4. 'Zig Zag' has a very low, tight, fine textured mound of green foliage, while 'Blonde Ambition' has taller, looser mounds of blue-green foliage.

BRIEF DESCRIPTION OF THE PHOTOGRAPHS

The accompanying color photographs illustrate the overall, typical appearance of the new and distinct plant showing the colors as true as it is reasonably possible to obtain in colored reproductions of conventional photography. Due to color variation reproduced in the photographs, color characteristics of this new variety should be determined with reference to the observations described herein, rather than a reliance on the photographs alone. The different photographs are intended to represent the distinctive characteristics of 'Zig Zag'. The photographs were taken in 2020 and depict plants that were 2 years of age, located in Santa Fe, NM.

FIG. 1 demonstrates growth habit and overall appearance of the plant.

Figure 2:
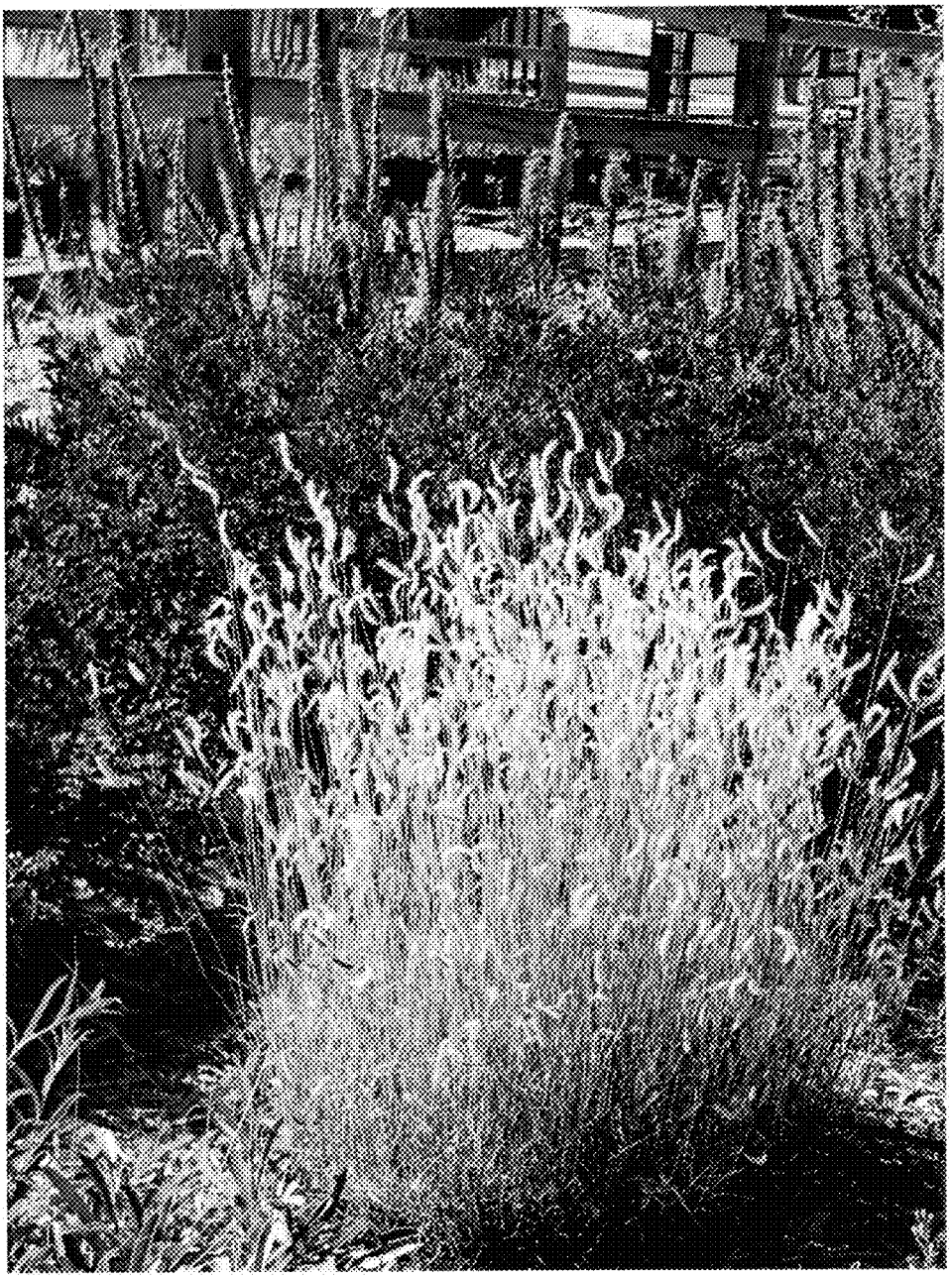

FIG. 2 demonstrates more elongated height of the plant.

DETAILED BOTANICAL DESCRIPTION

The present invention relates to a new and distinct *Bouteloua* hybrid plant. The following is a detailed description of the new variety 'Zig Zag'. Characteristic data were collected in the summer and fall of 2021 on plants grown in Santa Fe, NM and Davis, CA. Color references are made to the Munsell Color System. The age of the plant(s) used for measurements: 1-3 years.

Classification:

*Botanical*.—*Bouteloua* hybrid.

*Common*.—Blue Grama Grass.

Plant:

*Type*.—Herbaceous grass.

*Duration*.—Perennial.

*Ploidy*.—Diploid.

*Cold tolerance*.—USDA 4 to 8.

*Optimal temperature range*.—Tolerant of a wide range of growing temperatures including triple digit summer heat and subzero winter cold.

*Blooming period*.—Late summer to fall (as observed in Santa Fe, New Mexico, United States located at 35.6870° N, 105.9378° W).

*Growth habit*.—Loosely caespitose, stoloniferous, flowering stems erect, numerous (150-400 in vigorous, 3-year-old plants).

*Height, unpruned* (*average*).—25-40 cm.

*Spread* (*average*).—Stoloniferous, spreading outward by ~1 cm per month during the growing season; vigorous, three-year-old plants with bases 25-35 cm in diameter.

*Roots*.—Fibrous and fine, deeply rooted, roots 0.4-0.6 mm in diameter, pale brown (2.5Y 7/4 to 6/4).

*Pest resistance*.—Per a Landscape Plant Irrigation Trial the claimed variety scored an average 4.7-4.8 from May to October in 2023. On a scale from 1-5, 5 indicates the highest quality rating indicating no visible damage and 1 indicates the lowest quality rating indicating plants are severely damaged and probably dying (>75% affected).

*Disease resistance*.—Per a Landscape Plant Irrigation Trial the claimed variety scored an average 5.0 from May to October in 2023. On a scale from 1-5, 5 indicates the highest quality rating indicating no visible damage and 1 indicates the lowest quality rating indicating plants are severely damaged and probably dying (>75% affected).

Stolons: 1.5-2.5 mm thick, internodes 1-3 mm long, new growth glaucous, with a thin whitish coating that is soon lost; pale green (5GY 7/6 to 6/4) when young, aging pale brown (2.5Y 7/4 to 6/4), rooting throughout their lengths; glabrous except for small pilose tufts at the base of the prophyll (first leaf on each stolon); this and all other pubescence translucent, colorless. Prophylls 9-14 mm long, 2.5-3 mm wide near the base, tapering gradually to the acute apex, prominently two-keeled, pale brown (2.5Y 7/6 to 6/4) when mature, glabrous except for the keels, which are densely pilose in the proximal ~1/3, trichomes ~1 mm long. Scales (leaves of the stolons) 10-18 mm long, 2.5-3 mm wide near the base, with 10-13 veins, midvein slightly enlarged; bases encircling the stolon but otherwise loosely appressed and not sheathing; not differentiated into a sheath and blade; pale brown (2.5Y 7/6 to 6/4) at maturity; glabrous throughout or weakly antrorsely scabrous on the margins distally; scabrosities translucent, colorless, more or less conical, straight or slightly incurved, ~0.5 mm long and at a ~45° angle to the margin (subsequent scabrous parts also following this description).

*Culms* (*stems*).—Cylindrical, 0.7-1 mm diameter, 10-22 cm tall (measured to the highest node); ~10-ribbed, glabrous, smooth, mostly obscured by the sheaths of the leaves; green (7.5GY 7/6 to 6/6), aging pale tan (5Y 8/4 to 7/4). Prophylls (first leaf of each culm) like those of the stolons but smaller (8-11 cm×~2 mm). Culms often with 1-2 scales above the prophyll, these also like those of the stolons but smaller (8-11 cm×~2 mm). Culms usually with 3-4 cauline leaves. Internodes lengthening up the culm, from 3-10 cm long.

Leaves: 2-5 basal leaves per culm and 4-8 cauline leaves per culm, both with a sheathing basal portion, a spreading blade, and a ligule arising at the junction of the sheath and blade. Ligule a translucent/colorless ciliate membrane ~1 mm long, ~1.5 mm wide, cleft into cilia about half its length. Basal and cauline leaves poorly differentiated. Culms often forked, usually immediately above the basal leaves but sometimes more distally.

*Basal leaves*.—Sheaths 1.4-4 (–6) cm long, 0.8-1.2 mm in diameter, with ~10 veins much like the ribs of the stems, midvein greatly enlarged proximally, becoming less prominent distally; glabrous; green (7.5GY 7/6 to 6/6), aging pale tan (5Y 9/4 to 8/4). Bases are rounded. Blades flat (or rolled if plants are stressed), spreading and gently arced, simple, entire, linear, gently tapered to an acute apex; 2.5-4.5 (–6.5) cm long, 1.5-2 mm wide, ~0.1 mm thick; weakly antrorsely scabrous on the margins, glabrous on both surfaces or sparsely scabrous on the veins adaxially; green (7.5GY 6/8 to 5/8), aging pale tan (5Y 9/4 to 8/4), on both upper and lower surfaces. Blades 7-13-veined, all veins about equally prominent;

adaxial blade surface nearly plane, the veins only slightly raised; abaxial surface ridged, the veins about twice as thick as the spaces between them; spaces between the veins slightly translucent. Cauline leaves with sheaths 3-6 cm long and blades 4-12 cm long, typically glabrous on both surfaces but occasionally sparsely scabrous adaxially on the veins, otherwise like the basal. Cauline leaf sheaths 0.6-1.2 mm in diameter, averaging 1 mm at mid-culm, pale green (7.5GY 9/6 to 8/6) basally and darkening to green (7.5GY 7/6 to 6/6) distally, aging pale tan (5Y 9/2 to 8/4). Cauline leaf blades 0.8-2 mm wide, averaging 1.5 mm wide at mid-culm.

Inflorescence: A panicle of 1-2 unilateral, spicate primary branches terminating each culm, 12-27 cm tall (measured from uppermost node of the culm) and 2-3.5 cm wide. Upper branch at the apex of the central axis of the panicle, subtended by 2 (occasionally 1) small, erect bracts, each 4-8 mm×0.5-0.8 mm; lower branch, when present, 2.5-4 cm below the upper and usually on the opposite side of the central axis.

*Branches*.—Broadly linear, 22-36 mm long and 4.5-6 mm tall (as viewed laterally); straight and usually ascending at a ~45° angle to the stem at anthesis, becoming more erect and curving gently toward the stem with age. Inflorescence branches usually appearing two-toned at anthesis, adaxially dull rose (10RP 3/4) and abaxially pale green (5GY 8/4).

*Rachis*.—Of each branch divided into a short (2.5-3 mm) proximal portion without spikelets and a much longer (20-34 mm) distal portion bearing spikelets. The short, proximal portion of the rachis terete to slightly flattened; densely pubescent abaxially with minute acicular trichomes, these perpendicular to the surface of the rachis at their bases but weakly recurved distally, about the same length as the scabrosities elsewhere on the plant but narrower; minute acicular trichomes sparser adaxially and joined by pilose trichomes to ~1.5 mm long. Distal, spikelet-bearing portion of the rachis dorsoventrally flattened, 0.6-0.8 mm×~0.1 mm near the base, gradually tapering to 0.3-0.5 mm wide near the apex, with a thickened and darkened nerve near each edge; scabrous on the margins, otherwise glabrous. Green (7.5GY 5/6 to 4/8).

Spikelets: 55-75 per primary branch, appearing sessile on the abaxial side of the rachis but each borne on a minute, scabrous pedicel, ~0.5 mm long and diverging from the marginal vein of the rachis at a 5-10° angle; arising alternately from the nerves along the edges of the rachis, ascending at a 45-60° angle to the rachis at anthesis, usually spreading more widely as the inflorescences age; 6-7.5 mm in length (excluding the dangling stamens). Each spikelet with two glumes, one fertile floret (with all parts well-developed, if not reproductively competent), and 1-2 reduced florets; terminal spikelet smaller, 3-4 mm, often erect and looking superficially like a continuation of the rachis, often with fewer florets or these only partially developed. Yellow-green (2.5GY 8/2 to 5GY 7/2).

*Glumes*.—Bases rounded and apices acuminate to awn-tipped. First glumes on the inward side of each spikelet, not or scarcely visible on intact branches of the inflorescence, pale and nearly colorless (5Y 9/2 to N9), 3-4 mm long, conduplicate, narrowly lanceolate, ~0.4 mm wide near the base (when flattened), apex acuminate, midnerve thickened but not darkened, scabrous. Second glumes on the outward side of each spikelet, 5-6.5 mm long, conduplicate, narrowly lanceolate, 0.8-1 mm wide near the base (when flattened), apex acuminate, midnerve thickened and scabrous, often a little darkened, glume otherwise scarious and typically dull rose (10RP 2/4 to 3/4) in plants getting ample sunlight, to pale green (5GY 7/6 to 6/4) with less sun. Second glumes scabrous on the keels; with a tuft of 5-10 pustulose-based, spreading trichomes ~2.5 mm long on the base of the midnerve, the bases joined into an irregular mass ~0.2 mm across; 4-7 more pustulose-based trichomes scattered along ½ to ⅔ the length of the midnerve.

*Fertile floret*.—Lemma ~6 mm long, conduplicate, narrowly lanceolate, 3-nerved, ~1 mm wide near the base (when flattened). Bases rounded to broadly acute, apices prolonged into terminal awns. Central nerve prolonged into a scabrous awn 1.5-2 mm, flanked by two acuminate, scarious lobes ~0.6 mm long; lateral nerves each prolonged into 1.5-2 mm long, erect awns from about the middle of the lemma's length; proximal half or so of the midnerve pilose with trichomes ~1 mm long, scabrous distally. Lemma body pale and nearly colorless (5Y 9/2 to N9), awns either the same color or pale green (5GY 8/6 to 7/4). Palea pale and nearly colorless, 2-keeled, 3.5-4 mm×~0.5 mm, bifurcated apically into two short, weak awns ~0.5 mm long, keels and awns scabrous. Androecium of 3 stamens; filaments 6-7 mm long; anthers dangling just below the tips of the glumes, chartreuse (5GY 8/8) to pale yellow (10Y 9/4), 2.3-3 mm×0.5-0.8 mm, thecae connate about ⅔ of their length but diverging basally, the filament inserted in the notch. Pollen irregularly spheroid, averaging ~30 μm in diameter, apparently not well-formed, having the appearance of partially deflated beach balls. Pollen abundant, translucent, colorless. Gynoecium with a narrowly ellipsoid ovary ~1 mm long; styles 2, ~0.5 mm long, each with a feathery stigma ~1.3×~0.5 mm. Plants apparently sterile, ovaries not enlarging after anthesis and well-formed seeds not seen. Ovary is greenish-white (5GY 9/2) at anthesis.

*Second floret* (*reduced*).—Borne on a ~1 mm rachilla, pale and nearly colorless throughout (5Y 9/2 to N9), or the awns darkening distally to pale green (5GY 8/6 to 7/4); lemma pilose basally, trichomes loosely spreading, ~2 mm long, lemma split nearly to the base into three scabrous awns 3.5-4 mm long; palea ~1 mm long, bifurcate nearly to base, scabrous; androecium & gynoecium absent, or androecium with vestigial anthers to 0.7 mm long.

*Third floret* (*reduced, sometimes absent*).—Borne on a ~0.5 mm rachilla; variable, either: lemma and palea both diaphanous, folded, having an inflated appearance, 1-1.5 mm long, pale and nearly colorless (5Y 9/2 to N9) or occasionally pale lavender (2.5P 7/4); or lemma and palea like those of the second floret, but ½ to ⅔ the size.

The invention claimed is:

1. A new and distinct variety of *Bouteloua* hybrid plant named 'Zig Zag' as described and illustrated herein.

* * * * *